United States Patent
Ito et al.

(10) Patent No.: US 12,275,681 B2
(45) Date of Patent: Apr. 15, 2025

(54) OLEFIN COMPOUND PRODUCTION METHOD

(71) Applicant: DAIKIN INDUSTRIES, LTD., Osaka (JP)

(72) Inventors: Yuuko Ito, Osaka (JP); Tsubasa Nakaue, Osaka (JP); Takehiro Chaki, Osaka (JP); Takashi Usui, Osaka (JP); Tomoyuki Iwamoto, Osaka (JP); Megumi Kushida, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 572 days.

(21) Appl. No.: 17/588,499

(22) Filed: Jan. 31, 2022

(65) Prior Publication Data

US 2022/0153664 A1    May 19, 2022

Related U.S. Application Data

(63) Continuation of application No. PCT/JP2020/029790, filed on Aug. 4, 2020.

(30) Foreign Application Priority Data

Aug. 6, 2019   (JP) .............................. 2019-144222

(51) Int. Cl.
   *C07C 17/35*   (2006.01)
(52) U.S. Cl.
   CPC .................... *C07C 17/35* (2013.01)
(58) Field of Classification Search
   CPC ........ C07C 17/35; C07C 21/18; C07F 9/5013
   See application file for complete search history.

(56) References Cited

U.S. PATENT DOCUMENTS

2017/0369402 A1    12/2017   Takahira

FOREIGN PATENT DOCUMENTS

WO    2016/140317    9/2016

OTHER PUBLICATIONS

Hayashi et al., (Chemical Society of Japan, 1979 pp. 983-986).*
English language translation of International Preliminary Report on Patentability issued Feb. 8, 2022 in corresponding International (PCT) Patent Application No. PCT/JP2020/029790.
Frohn et al., "The unusual reactivity of $C_3F_7OCF=CF_2$ with $PBu_3$ and the complex hydrides $M[EH_4]$ (M: Li, Na; E: B, Al); preparation of potassium perfluoro-2-propoxyeth-1-enyltrifluoroborate $K[C_3F_7OCF=CFBF_3]$", Journal of Fluorine Chemistry, vol. 123, 2003, pp. 43-49.
Burton et al., "Preparation of E-1,2,3,3,3-pentafluoropropene, Z-1,2,3,3,3-pentafluoropropene and E-1-iodopentafluoropropene", Journal of Fluorine Chemistry, vol. 44, 1989, pp. 167-174.
Frohn et al., "(Fluoroorgano) fluoroboranes and -fluoroborates. 2 Synthesis of Spectroscopic Characterization of Potassium Polyfluoroalken-1-yltrifluoroborates", Zeitschrift fuer Anorganische und Allgemeine Chemie, vol. 627, No. 11, 2001, pp. 2499-2505.
Donald J. Burton et al., "Wittig Olefination via Reaction of Fluorine-Containing Phosphoranium Salts and F-Acyl Fluorides. A New Approach to Fluoroolefin Synthesis[1]", Journal of the American Chemical Society, (1983), vol. 105, No. 3, pp. 650-651.
Yu. L. Yagupolskii et al., "Alternative synthetic routes to hydrofluoroolefins", Journal of Fluorine Chemistry, vol. 179, (2015), pp. 134-141.
Extended European Search Report issued Aug. 7, 2023 in corresponding European Patent Application No. 20850569.3.
International Search Report issued Sep. 8, 2020 in International (PCT) Application No. PCT/JP2020/029790.

* cited by examiner

*Primary Examiner* — Jafar F Parsa
(74) *Attorney, Agent, or Firm* — Wenderoth, Lind & Ponack, L.L.P.

(57) ABSTRACT

Provided is a method for producing an olefin compound using reaction with a base, whereby a target product with a higher purity than the prior art can be obtained. Specifically, provided is a method for producing an olefin compound by reacting a phosphorus-containing olefin compound salt with a base to obtain a dephosphorized and hydrogenated olefin compound, wherein the temperature of the reaction is 50° C. or less.

5 Claims, No Drawings

OLEFIN COMPOUND PRODUCTION METHOD

TECHNICAL FIELD

The present disclosure relates to a method for producing an olefin compound.

BACKGROUND ART (E)-1,2-difluoroethylene (hereinafter referred to as "R1132(E)") has a low global warming potential (GWP), and thus has attracted attention as an alternative refrigerant to difluoromethane (R-32) and 1,1,1,2,2-pentafluoroethane (R-125), which are greenhouse gases.

Conventionally, as a method for producing R1132(E), for example, NPL 1 has reported that a reaction product containing a target product can be obtained according to the following procedure (Abstract and "3.2. Reactions of olefin 1 with Pbu3," in particular, 3.2.2).

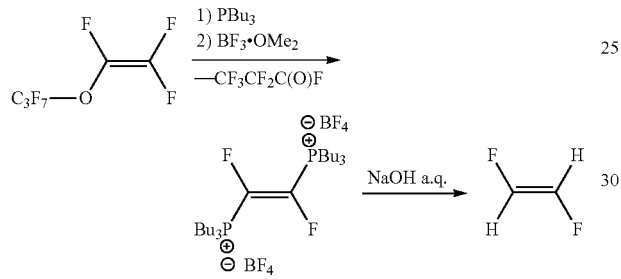

The above report example states that in addition to the target product R1132(E), about 16% (0.3 g for 1.9 g) of cis- and trans-1H-nonafluoro-2-propoxyethene (cis:trans=1:5) was also present as an impurity.

CITATION LIST

Non-Patent Literature

NPL 1: Journal of Fluorine Chemistry, 123 (2003) 43-49

SUMMARY

A method for producing an olefin compound, comprising reacting at least one phosphorus-containing olefin compound salt selected from the group consisting of:

a phosphorus-containing olefin compound salt A represented by the following formula (1):

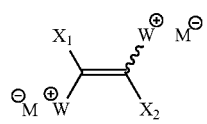

(1)

wherein $X_1$ and $X_2$ are each independently F, Cl, Br, I, or H; $W^+$s are the same or different and each is a monovalent cation comprising $PR_3$ or $P(OR)_3$, provided that Rs are groups having a saturated or unsaturated structure containing C and H, are optionally bonded together to form a ring, and optionally contain an atom other than C and H; three Rs included in $R_3$ and $(OR)_3$ are optionally the same or different; and $M^-$ is a monovalent anion comprising an atom or a compound;

a phosphorus-containing olefin compound salt B represented by the following formula (2):

(2)

wherein $X_1$, $X_2$, $W^+$, and $M^-$ are as defined above, and Y is F, Cl, Br, I, H, an alkyl group, an alkyl ether group, a fluoroalkyl group, or a fluoroalkyl ether group;

a phosphorus-containing olefin compound salt C represented by the following formula (3):

(3)

wherein $X_1$ and $X_2$ are as defined above, and Zs are the same or different and each is $P(=O)(OR)_2$, provided that Rs are groups having a saturated or unsaturated structure containing C and H, are optionally bonded together to form a ring, and optionally contain an atom other than C and H; and a phosphorus-containing olefin compound salt D represented by the following formula (4):

(4)

wherein $X_1$, $X_2$, Y, and Z are as defined above;
with a base, thereby obtaining a dephosphorized and hydrogenated olefin compound, wherein the temperature of the reaction is 50° C. or less.

Advantageous Effects

In the method for producing an olefin compound of the present disclosure, a specific phosphorus-containing olefin compound salt can be reacted with a base at a temperature of 50° C. or less, thereby producing a dephosphorized and hydrogenated olefin compound with high purity.

DESCRIPTION OF EMBODIMENTS

The method for producing an olefin compound of the present disclosure comprises reacting at least one phosphorus-containing olefin compound salt selected from the group consisting of:

a phosphorus-containing olefin compound salt A represented by the following formula (1):

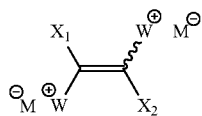
(1)

wherein $X_1$ and $X_2$ are each independently F, Cl, Br, I, or H; $W^+$s are the same or different and each is a monovalent cation comprising $PR_3$ or $P(OR)_3$, provided that Rs are groups having a saturated or unsaturated structure containing C and H, are optionally bonded together to form a ring, and optionally contain an atom other than C and H; three Rs included in $R_3$ and $(OR)_3$ are optionally the same or different; and $M^-$ is a monovalent anion comprising an atom or a compound;

a phosphorus-containing olefin compound salt B represented by the following formula (2):

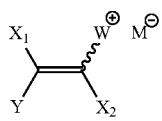
(2)

wherein $X_1$, $X_2$, $W^+$, and $M^-$ are as defined above, and Y is F, Cl, Br, I, H, an alkyl group, an alkyl ether group, a fluoroalkyl group, or a fluoroalkyl ether group;

a phosphorus-containing olefin compound salt C represented by the following formula (3):

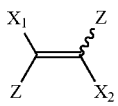
(3)

wherein $X_1$ and $X_2$ are as defined above, and Zs are the same or different and each is $P(=O)(OR)_2$, provided that Rs are groups having a saturated or unsaturated structure containing C and H, are optionally bonded together to form a ring, and optionally contain an atom other than C and H; and a phosphorus-containing olefin compound salt D represented by the following formula (4):

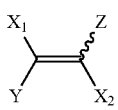
(4)

wherein $X_1$, $X_2$, Y, and Z are as defined above;
with a base, thereby obtaining a dephosphorized and hydrogenated olefin compound, wherein the temperature of the reaction is 50° C. or less.

According to the method for producing an olefin compound of the present disclosure, which has the above feature, a dephosphorized and hydrogenated olefin compound with high purity can be produced by reacting a specific phosphorus-containing olefin compound salt with a base at a temperature of 50° C. or less.

The phosphorus-containing olefin compound salt A is represented by the following formula (1):

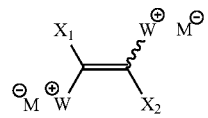
(1)

wherein $X_1$ and $X_2$ are each independently F, Cl, Br, I, or H; $W^+$s are the same or different and each is a monovalent cation comprising $PR_3$ or $P(OR)_3$, provided that Rs are groups having a saturated or unsaturated structure containing C and H, are optionally bonded together to form a ring, and optionally contain an atom other than C and H; three Rs included in $R_3$ and $(OR)_3$ are optionally the same or different; and $M^-$ is a monovalent anion comprising an atom or a compound.

$X_1$ and $X_2$ are each independently F, Cl, Br, I, or H. Of these, when the target olefin compound is R1132(E), $X_1$ and $X_2$ are both preferably F.

$W^+$s are the same or different and each is a monovalent cation comprising $PR_3$ or $P(OR)_3$, provided that Rs are groups having a saturated or unsaturated structure containing C and H, are optionally bonded together to form a ring, and optionally contain an atom other than C and H. That is, $W^+$s are cations of organic phosphine compounds.

Rs are groups having a saturated or unsaturated structure containing C and H, are optionally bonded together to form a ring, and optionally contain an atom other than C and H. Examples of a hydrocarbon group, which is a kind of the skeleton of this group, include alkyl, alkenyl, alkynyl, aryl, arylalkyl, and arylalkenyl groups, as well as hydrocarbon groups having a double or triple bond that satisfy the above requirements. These hydrocarbon groups may be bonded together to form a ring, and may have a substituent containing an atom other than C and H.

The number of carbon atoms in the above alkyl group, alkenyl group, and alkynyl group (hereinafter collectively referred to as the "alkyl group etc.") is not limited. The number of carbon atoms in the alkyl group is preferably 1 to 10, more preferably 1 to 8, even more preferably 1 to 6, and most preferably 1 to 4. Further, the number of carbon atoms in the alkenyl group and alkynyl group is preferably 2 to 10, more preferably 2 to 8, even more preferably 2 to 6, and most preferably 2 to 4. When the alkyl group etc. have a cyclic structure, the number of carbon atoms is preferably 4 to 12, more preferably 4 to 10, even more preferably 5 to 8, and most preferably 6 to 8.

The structure of the alkyl group etc. is not limited as long as the above requirements of Rs are satisfied. The alkyl group etc. may be linear or may have a side chain. The alkyl group etc. may have a chain structure or a cyclic structure (cycloalkyl group, cycloalkenyl group, or cycloalkynyl group). The alkyl group etc. may also have one or two or more substituents containing an atom other than C and H. In addition to such substituents, the alkyl group etc. may contain one or two or more atoms other than C and H in the chain structure or the cyclic structure. Examples of atoms other than C and H include one or two more of O, N, and S.

Examples of the alkyl group include methyl, ethyl, n-propyl, i-propyl, n-butyl, i-butyl, sec-butyl, t-butyl, pentyl, isopentyl, neopentyl, hexyl, heptyl, octyl, and 2-ethylhexyl groups. Examples of the cycloalkyl group include cyclopentyl, cyclohexyl, cycloheptyl, and 2-methylcyclohexyl groups. Examples of the alkenyl group include vinyl, allyl, and isopropenyl groups. Examples of the cycloalkenyl group include a cyclohexenyl group.

The number of carbon atoms in the above aryl group, arylalkyl group, and arylalkenyl group (hereinafter collectively referred to as the "aryl group etc.") is not limited. The number of carbon atoms is preferably 6 to 15, more preferably 6 to 12, and even more preferably 6 to 10.

The structure of the aryl group etc. is not limited as long as the above requirements of Rs are satisfied. The aryl group etc. may have one or two or more substituents. For example, the aromatic ring contained in the aryl group etc. may have one or two or more substituents. The position of the substituents may be any of o-, m-, and p-. Examples of the substituents include one or two or more of halogen atoms (e.g., fluorine, chlorine, and bromine atoms), alkyl groups, alkenyl groups, nitro groups, amino groups, hydroxyl groups, and alkoxy groups. When such a substituent is located on the aromatic ring, the position of the substituent may be any of o-, m-, and p-.

Examples of the aryl group include phenyl, tolyl, ethylphenyl, xylyl, cumenyl, mesityl, methoxyphenyl (o-, m-, and p-), ethoxyphenyl (o-, m-, and p-), 1-naphthyl, 2-naphthyl, and biphenylyl groups. Examples of the arylalkyl group include benzyl, methoxybenzyl (o-, m-, and p-), ethoxybenzyl (o-, m-, and p-), and phenethyl groups. Examples of the arylalkenyl group include styryl and cinnamyl groups.

Three Rs included in $PR_3$ and $P(OR)_3$ may be bonded together to form a ring. The structure of the ring is not limited. For example, the number of ring members can generally be 4 to 10, and preferably 5 to 8, including a phosphorus atom. The number of ring members is generally 5 or 6. The ring may contain heteroatoms (e.g., oxygen, nitrogen, and sulfur atoms) in its structure. Further, the ring may have other substituents. The ring may also have an unsaturated bond in its structure.

Three Rs included in $PR_3$ and $P(OR)_3$ may have the same or different structures.

$M^-$ is a monovalent anion comprising an atom or a compound.

Examples of the atom or compound that forms the anion include halogen ions, such as fluorine, chlorine, bromine, and iodine; carboxyl ions, such as formic acid, acetic acid, and oxalic acid; sulfonate ions, such as methanesulfonyloxy, trifluoromethanesulfonyloxy, benzenesulfonyloxy, and toluenesulfonyloxy; antimony fluoride ions; phosphorus fluoride ions; arsenic fluoride ions; boron fluoride ions; perchlorate ions; and the like. Of these, when the target olefin compound is R1132(E), boron fluoride ions are preferred.

The phosphorus-containing olefin compound salt B is represented by the following formula (2):

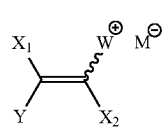

(2)

wherein $X_1$, $X_2$, $W^+$, and $M^-$ are as defined above, and Y is F, Cl, Br, I, H, an alkyl group, an alkyl ether group, a fluoroalkyl group, or a fluoroalkyl ether group.

The explanations of $X_1$, $X_2$, $W^+$, and $M^-$ are the same as those for the phosphorus-containing olefin compound salt A.

Y is F, Cl, Br, I, H, an alkyl group, an alkyl ether group, a fluoroalkyl group, or a fluoroalkyl ether group.

The explanation of the alkyl group is the same as that of Rs (alkyl groups) in the phosphorus-containing olefin compound salt A.

Examples of the alkyl ether group include compounds with oxygen atoms bonded to Rs (alkyl groups) in the phosphorus-containing olefin compound salt A.

Examples of the fluoroalkyl group include compounds with fluorine atoms substituted on carbon atoms in any number and in any combination. Of these, preferred are $C_{1-4}$ compounds, and particularly preferred are $C_1$ compounds.

Examples of the fluoroalkyl ether group include compounds with an oxygen atom bonded to the fluoroalkyl group.

The phosphorus-containing olefin compound salt C is represented by the following formula (3):

(3)

wherein $X_1$ and $X_2$ are as defined above, and Zs are the same or different and each is $P(=O)(OR)_2$, provided that Rs are groups having a saturated or unsaturated structure containing C and H, are optionally bonded together to form a ring, and optionally contain an atom other than C and H.

The explanations of $X_1$ and $X_2$ are the same as those for the phosphorus-containing olefin compound salt A.

Zs are the same or different and each is $P(=O)(OR)_2$, provided that Rs are groups having a saturated or unsaturated structure containing C and H, are optionally bonded together to form a ring, and optionally contain an atom other than C and H.

Rs are groups having a saturated or unsaturated structure containing C and H, are optionally bonded together to form a ring, and optionally contain an atom other than C and H. Examples of a hydrocarbon group, which is a kind of the skeleton of this group, include alkyl, alkenyl, alkynyl, aryl, arylalkyl, and arylalkenyl groups, as well as hydrocarbon groups having a double or triple bond that satisfy the above requirements. These hydrocarbon groups may be bonded together to form a ring, and may have a substituent containing an atom other than C and H.

The number of carbon atoms in the above alkyl group, alkenyl group, and alkynyl group (hereinafter collectively referred to as the "alkyl group etc.") is not limited. The number of carbon atoms in the alkyl group is preferably 1 to 10, more preferably 1 to 8, even more preferably 1 to 6, and most preferably 1 to 4. Further, the number of carbon atoms in the alkenyl group and alkynyl group is preferably 2 to 10, more preferably 2 to 8, even more preferably 2 to 6, and most preferably 2 to 4. When the alkyl group etc. have a cyclic structure, the number of carbon atoms is preferably 4 to 12, more preferably 4 to 10, even more preferably 5 to 8, and most preferably 6 to 8.

The structure of the alkyl group etc. is not limited as long as the above requirements of Rs are satisfied. The alkyl group etc. may be linear or may have a side chain. The alkyl group etc. may have a chain structure or a cyclic structure (cycloalkyl group, cycloalkenyl group, or cycloalkynyl group). The alkyl group etc. may also have one or two or more substituents containing an atom other than C and H. In addition to such substituents, the alkyl group etc. may contain one or two or more atoms other than C and H in the chain structure or the cyclic structure. Examples of atoms other than C and H include one or two more of O, N, and S.

Examples of the alkyl group include methyl, ethyl, n-propyl, i-propyl, n-butyl, i-butyl, sec-butyl, t-butyl, pentyl, isopentyl, neopentyl, hexyl, heptyl, octyl, and 2-ethylhexyl groups. Examples of the cycloalkyl group include cyclopentyl, cyclohexyl, cycloheptyl, and 2-methylcyclohexyl groups. Examples of the alkenyl group include vinyl, allyl, and isopropenyl groups. Examples of the cycloalkenyl group include a cyclohexenyl group.

The number of carbon atoms in the above aryl group, arylalkyl group, and arylalkenyl group (hereinafter collectively referred to as the "aryl group etc.") is not limited. The number of carbon atoms is preferably 6 to 15, more preferably 6 to 12, and even more preferably 6 to 10.

The structure of the aryl group etc. is not limited as long as the above requirements of Rs are satisfied. The aryl group etc. may have one or two or more substituents. For example, the aromatic ring contained in the aryl group etc. may have one or two or more substituents. The position of the substituents may be any of o-, m-, and p-. Examples of the substituents include one or two or more of halogen atoms (e.g., fluorine, chlorine, and bromine atoms), alkyl groups, alkenyl groups, nitro groups, amino groups, hydroxyl groups, and alkoxy groups. When such a substituent is located on the aromatic ring, the position of the substituent may be any of o-, m-, and p-.

Examples of the aryl group include phenyl, tolyl, ethylphenyl, xylyl, cumenyl, mesityl, methoxyphenyl (o-, m-, and p-), ethoxyphenyl (o-, m-, and p-), 1-naphthyl, 2-naphthyl, and biphenylyl groups. Examples of the arylalkyl group include benzyl, methoxybenzyl (o-, m-, and p-), ethoxybenzyl (o-, m-, and p-), and phenethyl groups. Examples of the arylalkenyl group include styryl and cinnamyl groups.

Two Rs included in P(=O) (OR)$_2$ may be bonded together to form a ring. The structure of the ring is not limited. For example, the number of ring members can generally be 4 to 10, and preferably 5 to 8, including a phosphorus atom. The number of ring members is generally 5 or 6. The ring may contain heteroatoms (e.g., oxygen, nitrogen, and sulfur atoms) in its structure. Further, the ring may have other substituents. The ring may also have an unsaturated bond in its structure. Furthermore, two Rs included in P(=O) (OR)$_2$ may have the same or different structures.

The phosphorus-containing olefin compound salt D is represented by the following formula (4):

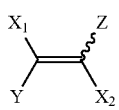
(4)

wherein $X_1$, $X_2$, Y, and Z are as defined above.

The explanations of $X_1$, $X_2$, Y, and Z are the same as those for the phosphorus-containing olefin compound salts A and C.

The phosphorus-containing olefin compound salts A to D may be those that can be dephosphorized and hydrogenated by reaction with a base to produce a target olefin compound. For example, in the production process of R1132(E) as shown below:

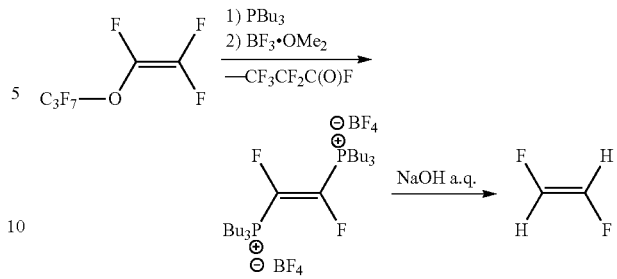

the phosphorus-containing olefin compound salt to be reacted with the base is one of the specific examples of the phosphorus-containing olefin compound salt A in the present disclosure. For example, in the production process of R1132 (E), the phosphorus-containing olefin compound salt (crystal) may contain at least one impurity selected from the group consisting of (trans-2-perfluoropropoxy-1,2-difluoroethen-1-yl) (tributyl) phosphonium tetrafluoroborate, (cis-2-perfluoropropoxy-1,2-difluoroethen-1-yl) (tributyl) phosphonium tetrafluoroborate, and perfluoropropoxy vinyl ether. If necessary, some or all of these impurities may be removed by recrystallisation or other purification methods before the reaction between the phosphorus-containing olefin compound salt and the base.

The method for producing an olefin compound of the present disclosure comprises reacting at least one of the phosphorus-containing olefin compound salts A to D with a base, thereby obtaining a dephosphorized and hydrogenated olefin compound, wherein the temperature of the reaction is 50° C. or less. The temperature of the reaction means that the temperature is maintained at 50° C. or less from the start to the end of the reaction with the base. The temperature of the reaction is preferably 15° C. or more and 50° C. or less, and the upper limit thereof is more preferably 40° C. or less.

According to the production method of the present disclosure, the production as by-products of trifluoroethylene, pentafluoroethane (R-125), 1,1,1,2-tetrafluoroethane (R-134a), etc. can be suppressed to increase the purity of the target product. When the temperature of the reaction is 40° C. or less, this effect is more likely to be obtained.

In the production method of the present disclosure, the reaction pressure is not limited, but is preferably set to 0.6 MPa or less, and more preferably about −0.1 to 0 MPa. Within such a pressure range, the reaction gas containing the target olefin compound can be prevented or suppressed from being dissolved in the reaction liquid. The pressure in the present specification refers to gauge pressure, unless otherwise specified.

In the present disclosure, when a phosphorus-containing olefin compound salt is reacted with a base, in order to suppress unnecessary heat generation, it is preferable to react the phosphorus-containing olefin compound salt with the base in a solvent or a dispersion medium. As a result, they can be reacted while efficiently removing heat from the reaction. Examples of the solvent or dispersion medium include water, tetrahydrofuran, 1,4-dioxane, dimethyl sulfoxide, and the like. Further, as a base solution, for example, 20 to 48 mass % aqueous solutions of various bases, such as sodium hydroxide, potassium hydroxide, and ammonia, can be suitably used. The use of various bases in this concentration range (in particular, 20 to 25 mass %) can increase the efficiency of removing heat from the reaction.

In the present disclosure, when the phosphorus-containing olefin compound salt is at least one of the phosphorus-containing olefin compound salt A and the phosphorus-containing olefin compound salt C, the target olefin compound is represented by the following formula (5):

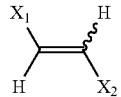

(5)

wherein $X_1$ and $X_2$ are as defined above.

Further, when the phosphorus-containing olefin compound salt is at least one of the phosphorus-containing olefin compound salt B and the phosphorus-containing olefin compound salt D, the target olefin compound is represented by the following formula (6):

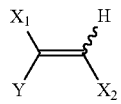

(6)

wherein $X_1$, $X_2$, and Y are as defined above.

In the present disclosure, the target olefin compound is preferably at least one member selected from the group consisting of (E)-1,2-difluoroethylene, trifluoroethylene, 1,3,3,3-tetrafluoropropene, and 1,1-difluoroethylene, all of which are included in the above formula (5) and/or (6), and particularly preferably (E)-1,2-difluoroethylene (R1132(E)).

Embodiments of the present disclosure are described above; however, the present disclosure is not limited to these examples. Of course, the present disclosure can be carried out in various forms without departing from the gist thereof.

As described above, the present disclosure includes the following.

1. A method for producing an olefin compound, comprising reacting at least one phosphorus-containing olefin compound salt selected from the group consisting of:

a phosphorus-containing olefin compound salt A represented by the following formula (1):

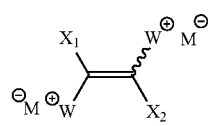

(1)

wherein $X_1$ and $X_2$ are each independently F, Cl, Br, I, or H; $W^+$s are the same or different and each is a monovalent cation comprising $PR_3$ or $P(OR)_3$, provided that Rs are groups having a saturated or unsaturated structure containing C and H, are optionally bonded together to form a ring, and optionally contain an atom other than C and H; three Rs included in $R_3$ and $(OR)_3$ are optionally the same or different; and M is a monovalent anion comprising an atom or a compound;

a phosphorus-containing olefin compound salt B represented by the following formula (2):

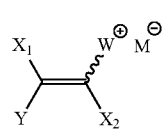

(2)

wherein $X_1$, $X_2$, $W^+$, and $M^-$ are as defined above, and Y is F, Cl, Br, I, H, an alkyl group, an alkyl ether group, a fluoroalkyl group, or a fluoroalkyl ether group;

a phosphorus-containing olefin compound salt C represented by the following formula (3):

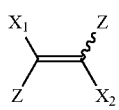

(3)

wherein $X_1$ and $X_2$ are as defined above, and Zs are the same or different and each is $P(=O)(OR)_2$, provided that Rs are groups having a saturated or unsaturated structure containing C and H, are optionally bonded together to form a ring, and optionally contain an atom other than C and H; and a phosphorus-containing olefin compound salt D represented by the following formula (4):

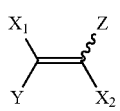

(4)

wherein $X_1$, $X_2$, Y, and Z are as defined above;
with a base, thereby obtaining a dephosphorized and hydrogenated olefin compound, wherein the temperature of the reaction is 50° C. or less.

2. The method for producing an olefin compound according to Item 1, wherein the temperature of the reaction is 15° C. or more and 50° C. or less.

3. The method for producing an olefin compound according to Item 1 or 2, wherein in the reaction, the phosphorus-containing olefin compound salt is reacted in a solvent or a dispersion medium.

4. The method for producing an olefin compound according to any one of Items 1 to 3, wherein the phosphorus-containing olefin compound salt is at least one of the phosphorus-containing olefin compound salt A and the phosphorus-containing olefin compound salt C, and the olefin compound is represented by the following formula (5):

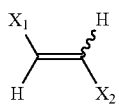

(5)

wherein $X_1$ and $X_2$ are as defined above.

5. The method for producing an olefin compound according to any one of Items 1 to 3, wherein the phosphorus-containing olefin compound salt is at least one of the phosphorus-containing olefin compound salt B and the phosphorus-containing olefin compound salt D, and the olefin compound is represented by the following formula (6):

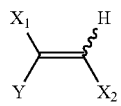

wherein $X_1$, $X_2$, and Y are as defined above.

6. The production method according to any one of Items 1 to 5, wherein the olefin compound is at least one member selected from the group consisting of (E)-1,2-difluoroethylene, trifluoroethylene, 1,3,3,3-tetrafluoropropene, and 1,1-difluoroethylene.

EXAMPLES

Embodiments of the present disclosure are described in more detail below based on Examples. However, the present disclosure is not limited to the scope of the Examples.

Example 1

100 parts by mass of a phosphorus-containing olefin compound salt represented by the following formula (7) was dispersed in 200 parts by mass of a solvent (water), and a 48% aqueous sodium hydroxide solution was added dropwise to cause a reaction. The reaction temperature was maintained in the range of 28 to 50° C., and the pressure in the reactor was maintained at 0 MPa or less, thereby producing R1132(E).

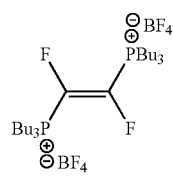

The results are shown in Table 1 below.

Example 2

R1132(E) was produced in the same manner as in Example 1, except that the reaction temperature was maintained at 22 to 40° C. The results are shown in Table 1 below.

Example 3

R1132(E) was produced in the same manner as in Example 1, except that the reaction temperature was maintained at 20 to 35° C., and the pressure in the reactor was maintained at 0.36 MPa or less. The results are shown in Table 1 below.

Example 4

R1132(E) was produced in the same manner as in Example 1, except that the reaction temperature was maintained constantly at 30° C. The results are shown in Table 1 below.

Example 5

R1132(E) was produced in the same manner as in Example 1, except that the reaction temperature was maintained at 20 to 35° C., and a 20% aqueous ammonia solution was used. The results are shown in Table 1 below.

Comparative Example 1

R1132(E) was produced in the same manner as in Example 1, except that the reaction temperature was maintained at 70° C., and no solvent was used. The results are shown in Table 1 below.

TABLE 1

| | Base | Reaction temperature (° C.) | Solvent | Reaction pressure (MPa) | GC (%) | | | | |
| | | | | | Acetylene | Trifluoroethylene | R1132 (E) | R-125 | R-134a | $C_4F_3H_3$ |
|---|---|---|---|---|---|---|---|---|---|---|
| Example 1 | 48% NaOH aq. | 28-50 | Water | −0.1-0 | 0.17 | 0.69 | 98.56 | 0.020 | 0.26 | 0.05 |
| Example 2 | 48% NaOH aq. | 22-40 | Water | −0.1-0 | 0.29 | — | 99.58 | — | — | 0.12 |
| Example 3 | 48% NaOH aq. | 20-35 | Water | −0.1-0.36 | 0.48 | 0.01 | 99.33 | — | 0.02 | 0.15 |
| Example 4 | 48% NaOH aq. | 30 | Water | −0.1-0 | 0.49 | — | 99.30 | — | — | 0.21 |
| Example 5 | 20% $NH_3$ aq. | 20-35 | Water | −0.1-0 | 0.68 | 0.026 | 98.85 | — | 0.045 | 0.40 |
| Comparative Example 1 | 48% NaOH aq. | 70 | — | — | — | 9.96 | 77.21 | 3.80 | — | — |

The invention claimed is:

1. A method for producing an olefin compound, comprising reacting at least one phosphorus-containing olefin compound salt selected from the group consisting of:
a phosphorus-containing olefin compound salt A represented by the following formula (1):

wherein $X_1$ and $X_2$ are each independently F, Cl, Br, I, or H; $W^+$s are the same or different and each is a monovalent cation comprising $PR_3$ or $P(OR)_3$, provided that Rs are groups having a saturated or unsaturated structure containing C and H, are optionally bonded together to form a ring, and optionally contain an atom other than C and H; three Rs included in $R_3$ and $(OR)_3$ are optionally the same or different; and $M^-$ is a boron fluoride ion;
a phosphorus-containing olefin compound salt B represented by the following formula (2):

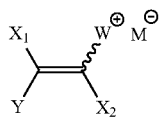 (2)

wherein $X_1$, $X_2$, $W^+$, and $M^-$ are as defined above, and Y is F, Cl, Br, I, H, an alkyl group, an alkyl ether group, a fluoroalkyl group, or a fluoroalkyl ether group;

a phosphorus-containing olefin compound salt C represented by the following formula (3):

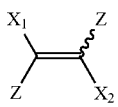 (3)

wherein $X_1$ and $X_2$ are as defined above, and Zs are the same or different and each is $P(=O)(OR)_2$, provided that Rs are groups having a saturated or unsaturated structure containing C and H, are optionally bonded together to form a ring, and optionally contain an atom other than C and H; and a phosphorus-containing olefin compound salt D represented by the following formula (4):

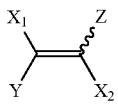 (4)

wherein $X_1$, $X_2$, Y, and Z are as defined above;

with a base, thereby obtaining a dephosphorized and hydrogenated olefin compound, wherein the temperature of the reaction is 15° C. or more and 50° C. or less.

2. The method for producing an olefin compound according to claim 1, wherein in the reaction, the phosphorus-containing olefin compound salt is reacted in a solvent or a dispersion medium.

3. The method for producing an olefin compound according to claim 1, wherein the phosphorus-containing olefin compound salt is at least one of the phosphorus-containing olefin compound salt A and the phosphorus-containing olefin compound salt C, and the olefin compound is represented by the following formula (5):

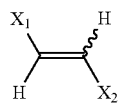 (5)

wherein $X_1$ and $X_2$ are as defined above.

4. The method for producing an olefin compound according to claim 1, wherein the phosphorus-containing olefin compound salt is at least one of the phosphorus-containing olefin compound salt B and the phosphorus-containing olefin compound salt D, and the olefin compound is represented by the following formula (6):

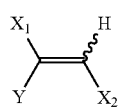 (6)

wherein $X_1$, $X_2$, and Y are as defined above.

5. The production method according to claim 1, wherein the olefin compound is at least one member selected from the group consisting of (E)-1,2-difluoroethylene, trifluoroethylene, 1,3,3,3-tetrafluoropropene, and 1,1-difluoroethylene.

* * * * *